United States Patent [19]

Luebke et al.

[11] Patent Number: 5,276,212
[45] Date of Patent: Jan. 4, 1994

[54] ETHERIFICATION WITH INTERMEDIATE SKELETAL OLEFIN ISOMERIZATION

[75] Inventors: Charles P. Luebke, Mount Prospect; Joseph E. Zimmermann, Arlington Heights, both of Ill.

[73] Assignee: UOP, Des Plaines, Ill.

[21] Appl. No.: 998,174

[22] Filed: Dec. 29, 1992

[51] Int. Cl.$^5$ .................. C07C 41/06; C07C 5/22
[52] U.S. Cl. .................... 568/697; 585/310; 585/314
[58] Field of Search .............. 568/697; 585/310, 314

[56] References Cited

U.S. PATENT DOCUMENTS

| | | | |
|---|---|---|---|
| 3,634,535 | 1/1972 | Haunschild | 260/677 A |
| 4,270,929 | 6/1981 | Dang Vu et al. | 44/56 |
| 4,282,389 | 8/1981 | Droste et al. | 568/697 |
| 4,330,679 | 5/1982 | Koehler et al. | 568/697 |
| 4,361,422 | 11/1982 | Derrien et al. | 44/56 |
| 4,513,153 | 4/1985 | Sandrin | 568/697 |
| 4,554,386 | 11/1985 | Groeneveld et al. | 568/697 |
| 4,581,474 | 4/1986 | Hutson, Jr. et al. | 568/697 |
| 4,778,943 | 10/1988 | Sun | 585/671 |
| 4,814,517 | 3/1989 | Trubac | 568/697 |
| 4,814,519 | 3/1989 | Harandi et al. | 568/697 |
| 4,950,803 | 8/1990 | Smith Jr. et al. | 568/697 |
| 5,008,455 | 4/1991 | Echleppinghoff | 568/697 |

Primary Examiner—Howard T. Mars
Attorney, Agent, or Firm—Thomas K. McBride; John G. Tolomei

[57] ABSTRACT

A combination of an etherification process and a process for the isomerization of linear alkenes to isoalkenes uses a first etherification zone that passes an etherification effluent and an etherification recycle stream through a skeletal isomerization separation zone to prepare an etherification feed for an additional etherification reactor. Etherification of additional isoalkane reactants in a separate etherification zone permits the production of additional ether products through isomerization without requiring additional etherification capacity upstream of the isomerization zone. Therefore additional etherification capacity can be added without significant changes to existing etherification capacity. The additional etherification zone may be in the form of a reactive distillation reactor that provides a high boiling ether product stream, a low boiling isoalkane vent stream and an intermediate boiling normal butene side-cut stream.

16 Claims, 1 Drawing Sheet

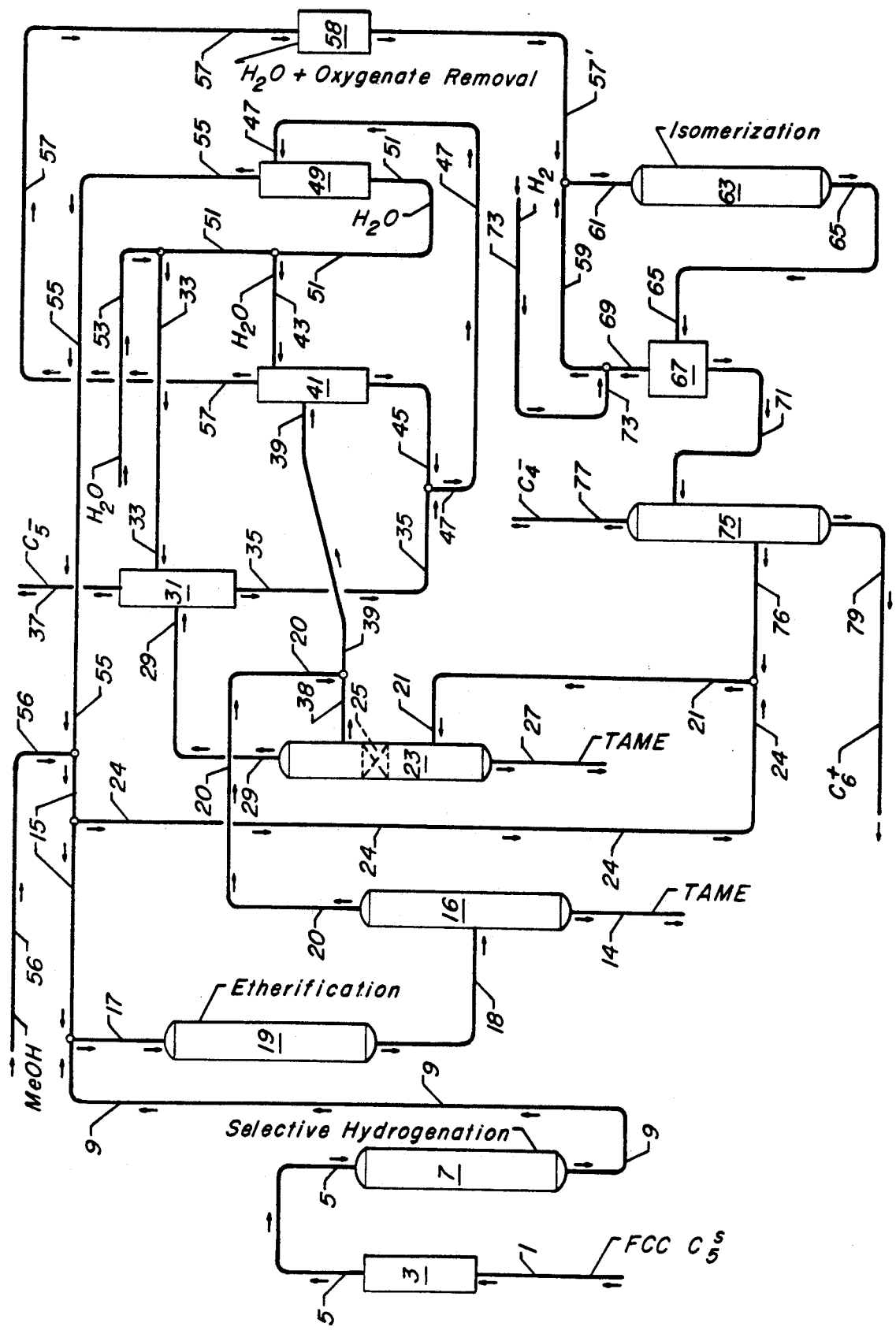

ETHERIFICATION WITH INTERMEDIATE SKELETAL OLEFIN ISOMERIZATION

FIELD OF THE INVENTION

This invention relates to processes for the production of ethers by the reaction of an alcohol with an isoolefin. More specifically this invention relates to a process for the production of ether and the skeletal isomerization of olefins to provide additional feedstock for the production of ethers.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and tertiary amyl methyl ether (TAME). These ethers have long been known as useful octane blending agents for gasoline motor fuels due to their high octane number (ROM) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. It has been known to increase the available feedstock by the dehydrogenation of paraffins and the skeletal isomerization of olefins. Methods for the dehydrogenation of paraffins, in particular isoparaffins, are well known in the art as are processes for the skeletal isomerization of normal olefins to isoolefins.

The use of isomerization to increase the isoolefins available for etherification requires the recycling of the isomerization effluent as feed to the etherification zone. Adding a recycle stream that includes normal alkenes and typically alkanes along with the additional isoalkenes increases the total mass flow rate to the etherification reactor. The higher mass flow to the etherification reactor can require an entirely new etherification reactor train due to inadequate capacity of the existing etherification reactors. In grass roots etherification addition, higher efficiency etherification reaction trains will use two reactors. An increased recycle adds to the cost the expense by increasing the size of two reactors.

An additional problem with etherification flow schemes is that the olefinic and paraffinic isomers of any given carbon number have relatively close boiling points. Separation of the isomers in an efficient manner to enhance the production of ether as well as the conversion of unreacted products to additional reactants has been difficult. Methods for the various separations have included adsorptive separations as well as extractive distillations. There is a need for etherification and isomerization process arrangements that simplify the separation of olefinic and paraffinic isomers to provide products and reactants and reduce the cost of recycling additional reactants for the production of ether.

SUMMARY OF THE INVENTION

This invention is an etherification process that uses a first etherification reactor to convert a fresh etherification zone feed and a second etherification reactor to convert unreacted components from the fresh feed and additional ether precursors from an isomerization zone that converts normal alkenes to isoalkenes in the first reaction zone. Etherification of additional isoalkene reactants in a separate etherification zone permits the production of additional ether products through isomerization without requiring additional etherification capacity upstream of the isomerization zone. Therefore additional etherification capacity can be added without significant changes to existing etherification capacity. The two etherification zones can operate integrally through the use of common methanol recovery facilities. Thus, this invention permits the addition of ether capacity in an arrangement having a reduced cost that can fully utilize existing etherification capacity.

In a preferred arrangement of this invention the additional etherification zone may be in the form of a reactive distillation reactor that provides a high boiling ether product stream, a low boiling isoalkane vent stream and an intermediate boiling normal butene side-cut stream. Thus this separation zone separates the higher boiling ether products from the lower boiling alcohols and isoparaffins while leaving an intermediate boiling stream that supplies linear alkenes to the skeletal olefin isomerization zone. The removal of the intermediate boiling stream concentrates a feedstream of linear alkenes to the reaction zone for the skeletal isomerization of the normal alkenes to isoalkenes. By taking the feedstream as an intermediate boiling cut, isoparaffins are rejected and linear alkenes are recycled while maintaining a low mass flow through the isomerization zone. Rejection of the isoparaffins from the feedstream eliminates the need for a drag stream of paraffins that was often required to prevent build-up of such unreacted hydrocarbons in the recycle loop of the combined process. The overall smaller flow rate to the isomerization zone lowers the overall capital and operating cost of the unit while adding only additional minor cost to the distillation system for the combined process.

Accordingly in one embodiment this invention is a process for the production of ether from a feedstream including normal alkene, isoalkene, normal alkane and isoalkane isomers. The process comprises mixing an etherification zone feedstream comprising isoalkenes, normal alkenes, normal alkanes and isoalkanes with a $C_1$-$C_5$ monohydroxy alcohol to produce a combined feed and contacting the combined feed with an etherification catalyst in a first etherification zone at etherification conditions to react isoalkenes with the alcohol and produce a first etherification effluent stream comprising ether, alcohol, normal alkane, isoalkane, and normal alkene isomers The process separates ether from the first etherification effluent stream to provide an ether product stream and first recycle stream comprising alcohol, normal alkane, isoalkane and normal alkene isomers. The first recycle stream mixes with a second recycle stream to provide a combined recycle stream. Contact of the combined recycle stream with an isomerization catalyst at isomerization conditions in an isomerization reaction zone for the skeletal isomerization of normal alkenes to isoalkenes produces an isomerization zone effluent stream comprising isoalkenes withdrawn from the isomerization zone and passed, at least in part, with a $C_1$–$C_5$ monohydroxy alcohol to a second etherification reaction zone. The second etherification reaction zone contacts the isomerization zone effluent and the alcohol with an etherification catalyst at etherification conditions to provide a second etherification zone effluent. Ether separated from the second etherification effluent stream provides a second product stream comprising ether and the second recycle stream that comprises alcohol, normal alkane, normal alkene and isoalkane isomers. The process rejects alkane isomers from the second recycle stream and combines at least a portion of the second recycle stream with the first recycle stream to provide the combined recycle stream.

Additional aspects of this invention relate to the arrangements required for distillation of feedstreams, reaction zone locations and treatment zones. In particular, another aspect of this invention is the reaction of unsaturated $C_4$ hydrocarbon isomers to produce MTBE and the reaction of unsaturated $C_5$ isomers for the production of methyl tertiary amyl ether. Another aspect of this invention is to withdraw the intermediate boiling stream as a sidecut from a distillation zone.

BRIEF DESCRIPTION OF THE DRAWING

The FIG. shows a schematic illustration of a process of this invention showing the etherification zones, isomerization zone, distillation zone along with additional separators, and treating zones for the purification of the feedstream and product.

DETAILED DESCRIPTION OF THE INVENTION

This invention is broadly applicable to the production of a wide variety of ethers from a number of different feedstocks. The primary ethers for which this invention will be applied are tertiary, amyl and butyl ethers. The advantages of this invention are achieved when the feedstream includes a mixture of normal and branched alkene and alkane isomers. Where the etherification process is one for the production of butyl ethers, the typical feedstream will consist of a mixture of $C_4$ isomers comprising isobutane, isobutene, normal butane, 1-butene and 2-butene. where the process is one for the production of amyl ethers, the feedstream components will include 3, methyl-1-butene, isopentane, 1-pentene, 2,methyl-1-butene, normal pentane, trans-2-pentene, cis-2-pentene and 2, methyl-2-butene in a typical distribution of isomers. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are light cracked hydrocarbon streams from an FCC unit, or a $C_4$ stream from a steam cracker after butadiene extraction. The feedstream of mixed, branched, and normal alkenes and alkanes will enter through a first isomerization zone.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel may be sulfided or unsulfided. The process can also operate at a broad range of operating conditions including pressures of from 40 to 800 psig with pressures of between 50 and 300 psig being preferred and temperatures of from 70°–700° F. with temperatures of from about 120°–400° F. being preferred. Effective space velocities for the processes should be above 1 $hr^{-1}$ and preferably are above 5 with a range of from between 5 to 35 $hrs^{-1}$. It is typical in such processes to limit the amount of hydrogen to prevent the saturation of monoolefins such that there is less than 2 times the stoichiometric amount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than the stoichiometrically required amount of hydrogen. Additional information related to the selective hydrogenation of diolefinic hydrocarbons, and in particular, unconjugated diolefinic hydrocarbons, can be found in U.S. Pat. No. 4,695,560.

The feed to the process includes an alcohol to react with the isoolefin and produce the desired ether product. The alcohols that can be used are typically $C_1$–$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

The isoalkene as well as the normal alkene hydrocarbons will enter the etherification zone along with the alcohol. Contact with the etherification catalyst at etherification conditions will produce the ether product. A wide range of materials are known to be effective as etherification catalysts for the isoalkene reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art and include copolymers of sulfonyl fluorovinyl ether and fluorocarbons as described in U.S. Pat. No. 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 m²/g, a pore volume of 0.6-2.5 ml/g and a mean pore diameter of 40-1000 angstroms. It is contemplated that the subject process could be preformed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 700 psig, and a temperature between about 85 and about 210° F. Even in the presence of additional light materials, pressures in the range of 140 to 580 psig are sufficient. A preferred temperature range is from 100°-210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene and isopentene reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. Nos. 4,219,678 to Obenaus et al. and 4,282,389 to Droste et al. which are incorporated herein for this teaching.

The etherification zone operates selectively to principally convert only the isoolefins. Therefore, alkanes and normal alkenes pass through the etherification zone without any significant conversion to products or by-products. Thus, the etherification zone effluent together with the unreacted feed components provides a stream of ether product and normal and branched alkenes and alkane isomers. It is possible in accordance with this invention to directly charge the effluent stream from a first etherification along with a recycle stream of unreacted components directly to an additional etherification reactor. Preferably the effluent stream from the first etherification zone, with is often part of an existing etherification facility, will enter a separation zone before unreacted components pass to a second etherification reactor. The separation zone receiving the ether products, alcohol and unreacted alcohol from the first or existing etherification zone distills the product into two fractions. Similar to most separation systems for recovery of ethers, the product separation zone provides a high boiling fraction that principally contains the ether product. The remaining lower boiling components including alcohol, normal alkenes and alkanes that were not reacted in the first etherification zone undergo further separation for the recovery of alcohol and then enter the isomerization zone as part of the feed. Isoparaffins typically provide the lowest boiling constituent of the alkene and alkane isomers. The isoalkane isomers can be conveniently withdrawn as lower boiling fraction from the separation zone.

The effluent from the first etherification zone is admixed with an effluent from a second etherification reaction zone. Prior to combination with the first etherification zone effluent, a separation zone recovers the ether product from the second effluent. Like the first etherification zone effluent, alcohol is removed from the second effluent. Preferably the process combines both effluents before alcohol recovery. Those skilled in the art are familiar with the various azeotropes formed by the alcohol and the effluent components and can provide suitable means for such separations and recoveries. As anticipated for most cases, methanol will be the usual alcohol. Water washing provides the usual means for recovering methanol in such arrangements.

Following etherification and separation, the combined stream of unreacted hydrocarbons from the first and second effluents, referred to as a combined recycle fraction undergoes skeletal isomerization of the normal alkenes to produce additional isoalkenes for the etherification process. In order to maintain this catalyst stability in the isomerization zone, the streams contacting the catalyst may require removal of polar contaminants such as sulfur, nitrogen or oxygen compounds. Thus, in addition to processing for the recovery of methanol, the intermediate boiling fraction may also require additional purification for the removal of compounds that can poison the catalyst or interfere with the skeletal isomerization process. Compounds that are usually most harmful to the isomerization catalyst include water, oxygenate compounds and nitrogen compounds. The water and oxygenate compounds suppress the isomerization catalyst activity. The nitrogen compounds also affect the isomerization catalyst activity and results in a reduced activity. These nitrogen compounds are also poison to acidic ion exchange resins used for the etherification and thus are also beneficially removed prior to the etherification. A variety of methods are known to remove such compounds which include water washing, adsorption and extraction processes. Oxygenate compounds and nitrogen compounds can be removed by typical adsorbents for the removal of these contaminants which comprise zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such as dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

The normal alkene-rich input stream after purification enters the isomerization zone. Methods for converting the normal alkene components to isoalkene components by isomerization are well known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. Nos. 4,778,943 and 4,814,519. A preferred catalyst for the isomerization reaction zone of this invention is a non-zeolitic molecular sieve. Preferred forms of the non-zeolitic molecular sieve for this invention includes silicoaluminophosphates and a magnesium aluminophosphate. Suitable non-zeolitic catalysts such as the SAPO and MgGAPO are described in U.S. Pat. Nos. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 1 to 7, aids the process by suppressing the formation of carbon compounds on the catalyst. The isomerization process will typically operate over a broad range of conditions including temperatures of from 120°-1300° F. with temperatures in the range of 200°-1000° F. being preferred and temperatures in a range of 450 to 800 being particularly preferred. Pressures for the isomerization reaction will also vary over a wide range extending from atmospheric conditions to 700 psig, and preferably are in a range of 50 to 350 psig. Space velocities can also vary over a wide range from 0.5 to 100 $hr^{-1}$ with a preferred range of 1-5 $hr^{-1}$. The expected per pass conversion of normal alkenes to isoalkenes in the isomerization zone will generally reach at least 40% of the total combined feed entering the reaction zone and will more typically exceed 50%.

The effluent stream from the isomerization zone containing isoalkenes normally undergoes separation for the recovery of light gases including hydrogen; however it is possible to operate the isomerization zone at hydrogen levels that will not require a recycle of hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. The presence of light ends in the isomerization zone effluent passes this light material on to the etherification zone as uncondensibles that, when rejected from the etherification separation system, drag methanol into downstream facilities thereby causing corrosion problems and methanol loss. Heavy materials such as $C_6+$ hydrocarbons tend to foul or deactivate the etherification catalyst.

The effluent from the isomerization zone, after any separation, is admixed with the alcohol and passes to the second etherification zone. The return of the isomerization effluent to the second etherification reaction provides a loop that excludes the first etherification zone and incorporates components that are recycled through the process. Suitable etherification systems for the second etherification zone include all of the arrangements previously described. Operating conditions for the second etherification reaction zone are also within the same range as those first described. However, the second reaction zone may operate at a slightly lower temperatures to improve conversion. Products from the second etherification zone undergo separation in separate separation facilities for the recovery of the ether product. The remaining lower boiling components also undergo further separation for alcohol recovery and usually light ends rejection.

In a continuously circulating process of this invention, the normal alkanes must also find a path out of the process loop in order to prevent their build-up. Typically, this process arrangement will withdraw a portion of the normal alkanes with a low boiling fraction taken from a separation zone for the second etherification zone. Withdrawal of the normal alkanes with a low boiling fraction establishes an equilibrium concentration of normal alkanes that controls their build-up in the recycle loop of the invention. With the removal of the low boiling fraction there remains an intermediate boiling fraction that contains normal alkenes for recycle after isomerization. The cut point between the intermediate boiling fraction and the low boiling fraction is set to maximize the removal of the isoalkane hydrocarbons and minimize the loss of normal alkenes between the low boiling fraction and the intermediate fraction. The arrangement of the separation zone can consist of separate columns for ether recovery and splitting the remainder of the effluent into the low and intermediate fractions. Preferably the separation zone consists of a single distillation column with the low boiling point fraction taken as an overhead, the high boiling point ether fraction taken as a bottoms stream, and the intermediate boiling point fraction for recycle taken as a sidecut from the column. Removal of the sidecut stream presents little problem for a typical etherification arrangement that already uses a distillation column. The sidecut of the normal alkene rich stream is taken a few trays below the overhead and will normally require the addition of only a few trays to the distillation column. It has been found that only a minimal amount of the normal alkene hydrocarbons are lost with the overhead by the method of this method while still maintaining the equilibrium of normal alkanes circulating through the process at a reasonable level. The cut point between the high boiling fraction and the intermediate fraction is readily determined on the basis of maximizing the ether recovery. The separation between the low boiling fraction and the intermediate fraction is usually not critical when the ether is used for fuel blending purposes since the normal alkene and alkane hydrocarbons present in the intermediate stream are usually suitable gasoline components.

A useful arrangement for the second etherification and separation zones is a reactive distillation zone that contains a bed of etherification catalyst. The distillation zone can provide the additional etherification of unreacted isoalkanes, and thus minimize their concentration in the intermediate boiling sidecut stream. Therefore, the reactive distillation zone can be used as a combined reactor and separation zone with the removal of the intermediate boiling fraction from the combined reaction and distillation zone. Processes for the production of ether by catalytic distillation are well known to those skilled in the art and are taught in U.S. Pat. Nos. 3,634,535 and 4,950,803. The preferred arrangement introduces the feed to a point below a bed of catalyst within a distillation zone. The high boiling fraction is withdrawn from the higher boiling point region below the bed of catalyst while the intermediate boiling stream typically has a withdrawal point in the relatively lower boiling region above the bed of catalyst. Catalytic distillation for the production of ethers typically employs the same operating conditions as those generally taught for etherification. No particular apparatus or arrangement is needed to retain the catalyst bed within the distillation zone and a variety of methods can be used to incorporate the bed or region of catalyst within the distillation zone. For example, catalyst may be retained between suitable packing materials or may be incorporated on to a distillation tray itself. A preferred method of retaining the catalyst is through the use of corrugated structural devices and is described in U.S. Pat. No. 5,073,236 which is hereby incorporated by reference.

Regardless of any additional splitting or reactive distillation the unreacted components from the second reaction zone undergo separation for the recovery of alcohol. The entire unreacted effluent portion from the second reaction zone may undergo alcohol removal by the previously described methods before any additional splitting. In order to minimize alcohol recovery facilities the unreacted effluent from the first etherification zone may also enter a common alcohol recovery zone with the entire unreacted fraction from the second etherification reaction zone. When the process uses reactive distillation separate alcohol recovery section are needed for the low boiling and intermediate boiling fractions.

The arrangement of this invention is best suited to the production of a single ether product. For example, in the case of MTBE or TAME, the separation of the second etherification zone effluent preferably extracts one group of normal alkanes as the isomers for withdrawal from the separation zone as the intermediate boiling product. In the case of a typical MTBE process, the high boiling fraction will comprise MTBE, the low boiling fraction will include methanol and isobutane, and the composition of the intermediate fraction includes primarily normal butane, 1-butene and 2-butene. Sidecut withdrawal is set to minimize the loss of 1-butene with the overhead while taking out sufficient normal butane with the overhead to maintain a reasonable level of normal butane in circulation through the process. Where the process is used for the production of TAME, the high boiling stream comprises the ether product, isopentane and lesser amounts of normal pentane comprise major components of the low boiling stream, and the intermediate boiling fraction contains the normal pentane and some isopentene isomers along with a substantial quantity of normal pentane that is maintained at a desired concentration level through the circulating $C_5$ hydrocarbons. In the pentene operation, the separation point between the low boiling and high boiling streams again seeks to maximize isopentane recovery while minimizing the loss of normal pentenes.

EXAMPLE 1

This invention is further described in the context of an example for the production of methyl tertiary amyl ether using a process or an arrangement as shown in the FIGURE. This example presents engineering calculations based on data from operating process units and laboratory test results. Relative flowing compositions for the major process streams of this Example are shown in Table 1 on a water-free basis. In this example, a feed comprising a $C_5$ cut from the product stream of a fluidized catalytic cracking unit enters the process through line 1 and passes through a water wash zone 3. Water wash zone 3 removes soluble nitrogen compounds and light oxygenates from the feed. Line 5 recovers the purified feed at a liquid flow of 7026 barrels per day and passes the feed to a selective hydrogenation reactor 7 for the removal of trace diolefin compounds. Line 9 carries the treated FCC feed which is saturated with water to a level of about 400 wppm and on a water-free basis has the relative flowing composition given in Table 1. Methanol in an amount of 748 lb-mol/hr carried by line 15 mixes with the $C_5$ feed carried by line 9 to provide an etherification feedstream passed by line 17 into an etherification reactor 19. Etherification reactor 19 contacts the combined feed with a sulfonated solid resin catalyst at a temperature of about 170° and a pressure of about 88 psig. Catalyst in etherification reactor 19 is arranged as a solid bed. A line 18 carries the effluent from etherification reactor 19 to a distillation column 16. Table 1 lists the relative composition of line 18. Distillation column withdraws 2150 barrels per day of tertiary amyl ether product through a bottom stream 14 and passes the remainder of the unreacted through an overhead stream 20 into admixture with an intermediate effluent 38 from a reactive distillation zone 23.

The second reactive distillation zone provides a second bed of sulfonated solid resin catalyst 25 located in an upper portion of the distillation column. A combined recycle feed and methanol from a line 24 transported by line 21 and having the feed composition given in the table enters column 23 at an average temperature of about 170° F. and a pressure of 88 psig. A bottoms stream 27 carries the tertiary methyl amyl ether product from the column and has the relative composition given in Table 1. An overhead stream 29 carried unreacted methanol and isopentane and lighter hydrocarbons from column 23. A portion of the overhead carried by line 29 is cooled, condensed and refluxed to the top of column 23 after separation of light gases in a condensing section (not shown). Line 29 carries the remainder of the effluent to a water wash column 31. Recycled and fresh water, entering column 31 from a line 33, carries methanol downward through the column where a line 35 takes the methanol along with the water. A $C_5$ drag stream in the form of the overhead line 37 leaves the top of water wash zone 31 and has the relative composition given in Table 1. Column 23 also the sidecut stream which is taken from a location above bed 25 by line 38. Line 39 transfers the sidecut stream and contents of line 20 to a water wash column 41 for the removal of methanol and other oxygenate streams. A line 43 charges water to the top of water wash column 41 which is collected by a line 45 and combined with the methanol and water from water wash column 31 into a stream 47. The contents of stream 47 enter a methanol separation column 49 for the recovery of water from the methanol stream. Water recovered from column 49 passes through a line 51 to supply water for column 41 through line 43 and is combined with make-up water from a line 53 to provide the water stream 33 for column 31. A line 55 carries methanol from the top of column 49 and combines it with fresh methanol entering by a line 56 to provide the methanol for the etherification through lines 15 and 24. Water washed hydrocarbons from methanol recovery column 41 pass overhead via line 57 and through a water and oxygenate removal zone 58 for the withdrawal of trace amounts of oxygenates such as dimethyl ether and water. Treatment of stream 57 in zone 58 lowers the concentration of water and water equivalent in line 57 to less than 30 wppm and yields a stream having the composition given in Table 1. The contents of line 57' are combined with a hydrogen recycle stream which is carried by line 59 to form a combined feed 61 that enters a reactor 63 for the skeletal isomerization of normal pentenes to isopentenes. Table 1 lists the composition of the hydrogen recycle stream carried by line 59. The combined feed enters the isomerization reaction zone at a temperature of about 120° F. and a pressure of about 290 psia. The combined feed contacts a silicoaluminophosphate catalyst of the SAPO-11 type within the reaction zone. Line 65 withdraws the product effluent from the isomerization reactor which passes through a liquid vapor separation zone 67. The liquid vapor separation zone recovers a hydrogen rich stream 69 which mixes with additional make-up hydrogen from line 73 to provide the hydrogen recycle stream 59. A line 71 transfers the heavier components from separator 67 to a distillation column 75. Column 75 fractionates light ends comprising $C_4^-$ materials overhead through a line 77 and drops $C_6^+$ components out of the process through a line 79. Line 76 carries the isopentene rich stream form column 75 into line 21 for completion of the recycle loop.

TABLE 1

| STREAM COMPOSITION - MOL % | | | | | | | |
|---|---|---|---|---|---|---|---|
| | Line 9 | Line 18 | Line 21 | Line 267 | Line 37 | Line 57 | Line 59 |
| $H_2$ | — | 1.39 | .57 | — | .04 | — | 91.51 |
| $C_1-C_4$ | 5.44 | 1.35 | 2.67 | .19 | 9.58 | .87 | .35 |
| 3M-1-butene | 1.68 | .55 | .88 | — | 2.25 | 1.03 | .06 |
| isopentane | 35.70 | 56.81 | 37.14 | .11 | 67.78 | 57.66 | 5.11 |
| 1-Pentene | 4.98 | .87 | 2.30 | .03 | 3.30 | 4.03 | .07 |
| 2M-1-Butene | 9.60 | 4.41 | .55 | .01 | .19 | .25 | .33 |
| Normal Pentane | 6.18 | 14.01 | 8.13 | 3.47 | 8.91 | 14.14 | 1.34 |
| Trans-2-Pentene | 9.23 | 4.07 | 5.27 | 1.68 | 3.93 | 10.38 | .26 |
| Cis-2-Pentene | 7.48 | 3.50 | 4.36 | 1.80 | 2.99 | 8.52 | .22 |
| 2M-2-Butene | 16.99 | 12.45 | 5.50 | .27 | 1.00 | 2.90 | .74 |
| $C_5$ Cyclic | 1.15 | .21 | .53 | 2.42 | .02 | .22 | |
| $C_6^+$ | 1.56 | .38 | .77 | 3.99 | | | |
| $H_2O$ wppm | 400 | 400 | 400 | 400 | 400 | 400 | 400 |
| Methanol | — | — | 20.08 | | | | |
| TAME | — | — | 11.23 | 86.03 | | | |

What is claimed is:

1. A process for the production of ether from a feedstream including normal alkene, isoalkene, normal alkane and isoalkane isomers, said process comprising:

(a) mixing an etherification zone feedstream comprising isoalkenes, normal alkenes, normal alkanes and isoalkanes with a $C_1-C_5$ monohydroxy alcohol to produce a combined feed and contacting said combined feed with an etherification catalyst in a first etherification zone at etherification conditions to react isoalkenes with said alcohol and produce a first etherification effluent stream comprising ether, alcohol, normal alkane, isoalkane, and normal alkene isomers;

(b) separating said ether from said first etherification effluent stream to provide a first recycle stream comprising alcohol, normal alkane, isoalkane and normal alkene isomers;

(c) mixing said first recycle stream with a second recycle stream to provide a combined recycle stream;

(d) contacting said combined recycle stream with an isomerization catalyst at isomerization conditions in an isomerization reaction zone for the skeletal isomerization of normal alkenes to isoalkenes;

(e) withdrawing an isomerization zone effluent stream comprising isoalkenes from said isomerization zone and passing at least a portion of said isomerization zone effluent and an $C_1-C_5$ monohydroxy alcohol to a second etherification reaction zone and contacting said isomerization zone effluent and said alcohol with an etherification catalyst at etherification conditions to provide a second etherification zone effluent;

(f) separating ether from said second etherification effluent stream to provide a second product stream comprising ether and said second recycle stream wherein said second recycle stream comprises alcohol, normal alkane, normal alkene and isoalkane isomers, (g) rejecting alkane isomers from said second recycle stream and combining at least a portion of said second recycle stream with said first recycle stream in accordance with step (c) to provide said combined recycle stream; and, (h) withdrawing said first and second product stream from the process.

2. The process of claim 1 wherein said combined recycle stream contains alcohol and said combined recycle stream passes through an alcohol recovery zone for the recovery of methanol.

3. The process of claim 1 wherein second etherification effluent passes to a distillation zone and said distillation zone separates said second distillation zone provides a high boiling fraction comprising ether and providing a said second product stream, a low boiling fraction comprising isoalkane that is rejected from said process, and an intermediate boiling fraction having an average boiling point between said low boiling and said high boiling fraction said intermediate fraction comprising normal alkene and normal alkane isomers and providing said second recycle stream.

4. The process of claim 1 wherein said isomers comprise $C_4$ or $C_5$ hydrocarbons and said alcohol comprises methanol or ethanol.

5. The process of claim 1 wherein said distillation zone contains a bed of etherification catalyst to provide said second etherification zone, said second product stream is withdrawn as a bottoms stream from said second etherification zone unreacted normal alkene and normal alkane isomers pass upwardly through said bed and said second recycle stream comprises normal alkene and normal alkane isomers that have passed through said bed.

6. A process for the production of tertiary amyl ether (TAME) from a feedstream including normal pentene, isopentene, normal pentane and isopentane isomers, said process comprising:

(a) mixing an etherification zone feedstream comprising isopentenes, normal pentenes isopentanes, and normal pentane with a $C_1-C_5$ monohydroxy alcohol to produce a combined feed and contacting said combined feed with an etherification catalyst in a first etherification zone at etherification conditions to react isopentenes with said alcohol and produce a first etherification effluent stream comprising ether, alcohol, isopentane, normal pentane and normal pentene isomers;

(b) separating said ether from said first etherification effluent stream to provide a first recycle stream comprising alcohol, normal pentane and normal pentene isomers;

(c) mixing said first recycle stream with a second recycle stream to provide a combined recycle stream and recovering alcohol from said combined recycle stream;

(d) contacting said combined recycle stream with an isomerization catalyst at isomerization conditions in an isomerization reaction zone for the skeletal isomerization of normal pentenes to isopentenes;

(e) withdrawing an isomerization zone effluent stream comprising isopentenes from said isomerization zone and passing at least a portion of said isomerization zone effluent and an $C_1$-$C_5$ monohydroxy alcohol to a reactive distillation zone and contacting said alcohol and isopentenes with an etherification catalyst at etherification conditions to produce a second etherification zone effluent stream that exits said reactive distillation zone as a bottoms stream and unreacted stream that exist said reactive distillation zone from a location above said catalyst bed;

(f) separating said unreacted stream into a rejected stream comprising material boiling at or below normal butane and second recycle stream comprising normal pentenes and normal pentane;

(g) combining at least a portion of said second recycle stream with said first recycle stream in accordance with step (c) to provide said combined recycle stream; and, (h) withdrawing said first and second product stream from the process.

7. The process of claim 6 wherein said alcohol comprises methanol and said product comprises a methyl tertiary amyl ether.

8. The process of claim 6 wherein at least one of said feedstream and said isomerization effluent is contacted with a selective hydrogenation catalyst at selective hydrogenation conditions in a selective hydrogenation zone to selectively saturate diolefins to monoolefins and isomerize isopentene double bonds.

9. The process of claim 6 wherein said distillation zone comprises a single reactive distillation column, said second ether product is withdrawn as bottoms stream, said unreacted stream is separated in an upper part of said column into an overhead stream comprising said rejected stream and a sidecut stream comprising said second recycle stream.

10. The process of claim 6 wherein said combined recycle stream is mixed with a hydrogen rich recycle stream before entering said isomerization zone and the concentration of water, and oxygenate compounds in said combined recycle stream is reduced to below 100 wppm of water equivalents before mixing said combined recycle stream with said hydrogen rich recycle stream.

11. The process of claim 6 wherein a relatively lighter fraction comprising $C_4$ and lower boiling hydrocarbons and relatively heavier fraction comprising $C_6$ a higher boiling hydrocarbons are separated from said isomerization effluent before it enters said reactive distillation zone.

12. A process for the production of tertiary butyl ether from a feedstream including normal butene, isobutene, normal butane, and isobutane, said process comprising:

(a) mixing an etherification zone feedstream comprising isobutene, normal butenes isobutane, and normal butane with a $C_1$-$C_5$ monohydroxy alcohol to produce a combined feed and contacting said combined feed with an etherification catalyst in a first etherification zone at etherification conditions to react isopentene with said alcohol and produce a first etherification effluent stream comprising tertiary butyl ether, alcohol, isobutane, normal butane and normal butene isomers;

(b) separating said ether from said first etherification effluent stream to provide a first recycle stream comprising alcohol, normal butane and normal butene isomers;

(c) mixing said first recycle stream with a second recycle stream to provide a combined recycle stream and recovering alcohol from said combined recycle stream;

(d) contacting said combined recycle stream with an isomerization catalyst at isomerization conditions in an isomerization reaction zone for the skeletal isomerization of normal butenes to isobutene;

(e) withdrawing an isomerization zone effluent stream comprising isobutene from said isomerization zone and passing at least a portion of said isomerization zone effluent and an $C_1$-$C_5$ monohydroxy alcohol to a reactive distillation zone and contacting said alcohol and isobutenes with an etherification catalyst at etherification conditions to produce a second etherification zone effluent stream that exits said reactive distillation zone as a bottoms stream and unreacted stream that exits said reactive distillation zone from a location above said catalyst bed;

(f) separating said unreacted stream into a rejected stream comprising material boiling at or below normal butane and a second recycle stream comprising normal butenes and normal butane;

(g) combining at least a portion of said second recycle stream with said first recycle stream in accordance with step (c) to provide said combined recycle stream; and, (h) withdrawing said first and second product stream from the process.

13. The process of claim 12 wherein said alcohol comprises methanol and said product comprises a methyl tertiary butyl ether.

14. The process of claim 12 wherein said feedstream is contacted with a selective hydrogenation catalyst at selective hydrogenation conditions in a selective hydrogenation zone to selectively saturate diolefins to monoolefins.

15. The process of claim 12 wherein said distillation zone comprises a single reactive distillation column, said second ether product is withdrawn as bottoms stream, said unreacted stream is separated in an upper part of said column into an overhead stream comprising said rejected stream and a sidecut stream comprising said second recycle stream.

16. The process of claim 12 wherein combined recycle stream is mixed with a hydrogen rich recycle stream before entering said isomerization zone and the concentration of water and oxygenate compounds in said combined recycle steam are reduced to below 100 wppm of water equivalents before mixing said combined recycle stream with said hydrogen rich recycle stream.

* * * * *

UNITED STATES PATENT AND TRADEMARK OFFICE
CERTIFICATE OF CORRECTION

PATENT NO. : 5,276,212
DATED : JANUARY 4, 1994
INVENTOR(S) : LUEBKE et al.

It is certified that error appears in the above-identified patent and that said Letters Patent is hereby corrected as shown below:

at column 14, line 9, "isopentene" is replaced with -- isobutene --.

Signed and Sealed this

Fourteenth Day of June, 1994

Attest:

BRUCE LEHMAN

Attesting Officer     Commissioner of Patents and Trademarks